(54) BIAXIALLY EXTENDIBLE MATERIAL

(75) Inventors: Michael Tod Morman, Alpharetta, GA (US); Lon M. Edelman, Alpharetta, GA (US); Reginald Smith, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 159 days.

(21) Appl. No.: 09/749,141

(22) Filed: Dec. 27, 2000

(65) Prior Publication Data

US 2002/0119288 A1 Aug. 29, 2002

(51) Int. Cl.⁷ .................................................. B32B 3/30
(52) U.S. Cl. ...................... 428/152; 428/141; 428/156; 428/181; 428/198; 442/182; 442/328
(58) Field of Search ................................. 428/141, 156, 428/152, 181, 198; 442/182, 328

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,668,054 A | 6/1972 | Stumpf |
| 3,692,618 A | 9/1972 | Dorschner et al. |
| 3,719,540 A | 3/1973 | Hall |
| 3,802,817 A | 4/1974 | Matsuki et al. |
| 3,849,241 A | 11/1974 | Butin et al. |
| 4,000,237 A | 12/1976 | Roberts, Jr. |
| 4,041,203 A | 8/1977 | Brock et al. |
| 4,158,594 A | 6/1979 | Becker et al. |
| 4,208,459 A | 6/1980 | Becker et al. |
| 4,340,563 A | 7/1982 | Appel et al. |
| 4,421,812 A | 12/1983 | Plant |
| 4,422,892 A | 12/1983 | Plant |
| 4,443,511 A | 4/1984 | Worden et al. |
| 4,443,513 A | 4/1984 | Meitner et al. |
| 4,606,964 A | 8/1986 | Wideman |
| 4,692,369 A | 9/1987 | Nomi |
| 4,701,176 A | 10/1987 | Wilson et al. |
| 4,704,114 A | 11/1987 | Wilson et al. |
| 4,710,187 A | 12/1987 | Boland et al. |
| 4,720,415 A | 1/1988 | Vander Wielen et al. |
| 4,756,709 A | 7/1988 | Stevens |
| 4,770,656 A | 9/1988 | Proxmire et al. |
| 4,777,073 A | 10/1988 | Sheth |

(List continued on next page.)

FOREIGN PATENT DOCUMENTS

| | | |
|---|---|---|
| WO | 92/16371 | 10/1992 |
| WO | 93/21013 | 10/1993 |

(List continued on next page.)

Primary Examiner—William P. Watkins, III
(74) Attorney, Agent, or Firm—Pauley Petersen Kinne & Erickson

(57) ABSTRACT

A biaxially extendible, breathable laminate having liquid barrier properties and low retractive force. The laminate includes a nonwoven web neck-stretched in a first direction to impart extendibility of the web in a second direction mutually perpendicular with the first direction, and a film that is extendible in the second direction. The film can be a breathable, microporous film, and can either be an inelastic film stretched to form rugosities in the second direction, or can be made of an extendible polymer that is extendible in the second direction. Using an appropriate elastomeric lamination and/or creping adhesive, the laminate is creped to produce extendibility in the first direction with some retractive force. The biaxial extendible laminate is particularly useful as an outer cover for diapers and other personal care products.

59 Claims, 2 Drawing Sheets

U.S. PATENT DOCUMENTS

| | | |
|---|---|---|
| 4,810,556 A | 3/1989 | Kobayashi et al. |
| 4,842,596 A | 6/1989 | Kielpikowski et al. |
| 4,891,258 A | 1/1990 | Fahrenkrug |
| 4,965,122 A | 10/1990 | Morman |
| 4,981,747 A | 1/1991 | Morman |
| 5,036,551 A | 8/1991 | Dailey et al. |
| 5,064,802 A | 11/1991 | Stevens et al. |
| 5,078,935 A | 1/1992 | Kobayashi et al. |
| 5,114,781 A | 5/1992 | Morman |
| 5,116,662 A | 5/1992 | Morman |
| 5,226,992 A | 7/1993 | Morman |
| 5,238,733 A | 8/1993 | Joseph et al. |
| 5,244,482 A | 9/1993 | Hassenboehler, Jr. et al. |
| 5,244,716 A | 9/1993 | Thornton et al. |
| 5,374,696 A | 12/1994 | Rosen et al. |
| 5,422,172 A | 6/1995 | Wu |
| 5,462,708 A | 10/1995 | Swenson et al. |
| 5,529,830 A | 6/1996 | Dutta et al. |
| 5,576,090 A | 11/1996 | Suzuki |
| 5,614,281 A | 3/1997 | Jackson et al. |
| 5,631,074 A | 5/1997 | Herlihy, Jr. |
| 5,656,167 A | 8/1997 | Martz |
| 5,704,101 A | 1/1998 | Majors et al. |
| 5,789,065 A | 8/1998 | Haffner et al. |
| 5,804,011 A | 9/1998 | Dutta et al. |
| 5,846,232 A | 12/1998 | Serbiak et al. |
| 5,851,935 A | 12/1998 | Srinivasan et al. |
| 5,861,074 A | 1/1999 | Wu |
| 5,865,926 A | 2/1999 | Wu et al. |
| 5,883,028 A | 3/1999 | Morman et al. |
| 5,885,908 A | 3/1999 | Jaeger et al. |
| 5,914,184 A | 6/1999 | Morman |
| 5,932,497 A | 8/1999 | Morman et al. |
| 5,958,555 A | 9/1999 | Takeuchi et al. |
| 6,015,764 A | 1/2000 | McCormack et al. |
| 6,020,535 A | 2/2000 | Blenke et al. |
| 6,028,240 A | 2/2000 | Wessel et al. |
| 6,045,900 A | 4/2000 | Haffner et al. |
| 6,069,097 A | 5/2000 | Suzuki et al. |
| 6,071,834 A | 6/2000 | Martz |
| 6,096,668 A | 8/2000 | Abuto et al. |
| 6,114,263 A * | 9/2000 | Benson et al. ............ 442/394 |
| 6,129,720 A | 10/2000 | Blenke et al. |
| 6,159,584 A | 12/2000 | Eaton et al. |
| 6,197,404 B1 | 3/2001 | Varona |

FOREIGN PATENT DOCUMENTS

| | | | |
|---|---|---|---|
| WO | 95/00097 | 1/1995 | |
| WO | WO 95/22951 | 8/1995 | |
| WO | WO 97/02133 | 1/1997 | |
| WO | 97/46198 | 12/1997 | |
| WO | 99/14262 | 3/1999 | |
| WO | 99/22619 | 5/1999 | |
| WO | 99/33425 | 7/1999 | |
| WO | 00/23273 | 4/2000 | |
| WO | WO 00/38911 | * | 7/2000 |
| WO | WO 00/38913 | * | 7/2000 |
| WO | 00/39201 | 7/2000 | |

* cited by examiner

BIAXIALLY EXTENDIBLE MATERIAL

FIELD OF THE INVENTION

This invention is directed to a material that is extendible in all x/y plane directions.

BACKGROUND OF THE INVENTION

A number of various material attributes are desirable for material used to make outer covers of absorbent articles. For example, in pant-like garments, machine direction extendibility is desirable because longitudinal conformability allows a crotch region of the garment to sag and bulge when loaded without pulling the waistband of the product down. Similarly, cross direction extendibility is desirable because lateral conformability maintains a snug, yet comfortable fit about a wearer's hips. Furthermore, extendibility in all directions in the x/y plane contributes to an all-around form-fitting product.

Some materials, such as necked stretch-bonded laminates (NSBL), necked/creped spunbond attached to elastomerics, etc., have all-direction stretch, i.e., elongation with power recovery. These materials are relatively expensive because of the inclusion of relatively expensive elastomeric materials. However, high recovery forces are not always desirable in outer cover materials. Low recovery forces allow the garments to remain in a conforming shape on the wearer without exerting a considerable amount of retractive pressure and without restricting a wearer's movements. Furthermore, when the garments are filled up by the wearer, low recovery forces allow the weight of the garment contents to pull the garment contents away from the wearer's body without pulling the rest of the garment down on the wearer's body, thereby maintaining close contact between the wearer and the garment in the waist area and around the leg openings to prevent leakage of any garment contents from the garment.

Breathability is a material attribute particularly desirable in absorbent articles. Breathable films and laminates typically block the passage of particulate matter, water and other liquids while allowing water vapor and/or air to pass through the material. Thus, breathable materials, when used in diapers or similar absorbent garments, reduce the relative humidity and temperature within the garment in comparison to such garments made of non-breathable films and laminates.

A liquid barrier is an inherently desirable material attribute of an absorbent article. The liquid barrier acts to prevent liquids from permeating through a surface of the garment and onto a wearer's clothing or surroundings.

Various types of material with combined attributes are known in the art. For example, stretch-bonded laminates (SBL) deliver a machine direction extendible, breathable composite, but have no liquid barrier and little extendibility in a cross direction. More recent neck-bonded laminates deliver a cross direction extendible liquid barrier, but are not extendible in the machine direction. Other composites function as cloth-like, breathable barriers, but they have little or no extendibility in either a machine direction or a cross direction.

U.S. Pat. No. 5,114,781 issued to Morman on May 19, 1992, discloses a laminate that can extend in at least two directions. The laminate includes a reversibly necked nonwoven material and an elastic sheet.

U.S. Pat. No. 5,116,662 issued to Morman on May 26, 1992, discloses a laminate that can extend in at least two directions. The laminate includes a necked nonwoven material and an elastic sheet.

U.S. Pat. No. 5,883,028 issued to Morman, et al., on Mar. 16, 1999, discloses a laminate that can extend in at least two directions. The laminate is formed by attaching a nonwoven material that is necked in the cross direction to a water vapor-soluble elastomeric film that is stretched in the machine direction and has retraction in the machine direction.

There is a need or desire for a material that delivers a multitude of properties in a single composite, namely biaxial extendibility, low recovery force, breathability, liquid barrier properties, and is relatively inexpensive.

SUMMARY OF THE INVENTION

The present invention is directed to an extendible outer cover (EOC) material that can extend in all x/y plane directions. In one embodiment, the EOC is a laminate including a necked nonwoven web and a striated, breathable, microporous film having striated rugosities in the machine direction. The striated rugosities allow the film and the necked nonwoven web to extend in the cross direction. The material of this embodiment is made by stretching the filled film in the machine direction to cause breathability, laminating the stretched film to the nonwoven web, stretching the laminate in the machine direction to neck the nonwoven web and form the striations in the film, then creping the laminate to create machine direction extendibility. An elastomeric lamination and/or creping adhesive can be used to produce a laminate with minor retractive force.

In another embodiment of the invention, the EOC is a laminate including a single-layer cross-direction extendible film made from an extendible polymer that permits the film, along with a necked nonwoven web bonded to the film, to extend in the cross direction. The material of this embodiment is made by stretching the filled film in the machine direction to cause breathability, separately stretching a nonwoven web to cause necking, laminating the stretched film and the necked nonwoven web together, then creping the laminate to create machine direction extendibility. As in the previous embodiment, an elastomeric lamination and/or creping adhesive can be used to produce a laminate with minor retractive force.

The adhesive add-on level and bond pattern greatly affect material properties. Thus, the resulting material of the invention can have a high retractive force in one direction and low or no retractive force in another. Further retractive force can be imparted in one or both directions through the addition of elastomeric film, fibers, foams, scrims, or other elements.

With the foregoing in mind, it is a feature and advantage of the invention to provide a biaxially extendible, breathable laminate having liquid barrier properties and low recovery force.

It is also a feature and advantage of the invention to provide an improved biaxially extendible, breathable laminate useful in a wide variety of diaper outer covers, other personal care products, surgical gowns, and other breathable applications.

The foregoing and other features and advantages of the invention will become further apparent from the following detailed description of the presently preferred embodiments, read in conjunction with the examples and drawings.

DEFINITIONS

Figure 1:
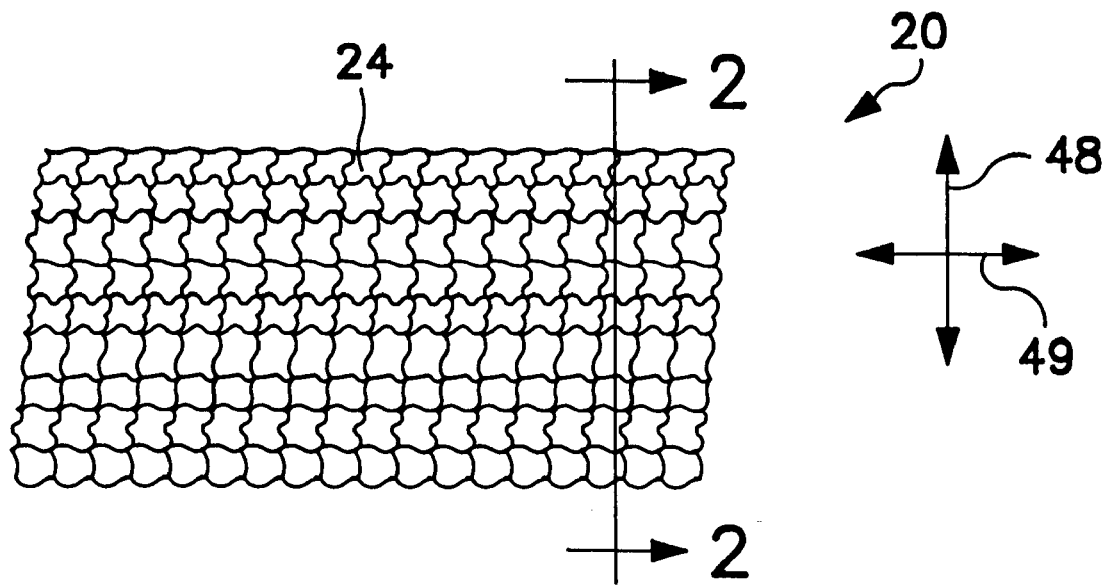
FIG. 1 is a top view of a biaxially extendible, breathable laminate of the present invention.

Within the context of this specification, each term or phrase below will include the following meaning or meanings.

"Biaxially extendible" refers to a material having extendibility by at least 25% of its initial dimensions (without rupture, tear or loss of barrier properties) in two directions perpendicular to one another, e.g. extendibility in a machine direction and in a cross direction, or in a longitudinal direction (front to back) and a lateral direction (side to side).

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Creped" or "Crepe" refers to a crinkled material or composite having bonded and unbonded areas. The creped material can be returned to approximately its original length by applying a mechanical stress, thus smoothing out the crinkled portions.

"Cross direction" refers to the width of a fabric in a direction generally perpendicular to the direction in which it is produced, as opposed to "machine direction" which refers to the length of a fabric in the direction in which it is produced.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extendible" means a material which, upon application of a stretching force, can be extended in a particular direction, to a stretched dimension (e.g., width) which is at least 25% greater than an original, unstretched dimension. When the stretching force is removed after a one-minute holding period, the material does not retract, or retracts by not more than 30% of the difference between the stretched dimension and the original dimension, and may retract more only if aided by an elastic adhesive or other elastic component bonded to the material. Thus, a material having a width of one meter, which is extendible in the cross direction, can be stretched to a width of at least 1.25 meters. When the stretching force is released, after holding the extended width for one minute, a material stretched to a width of 1.25 meters will not retract, or will retract to a width of not less than 1.175 meters. Extendible materials are different from elastic materials, the latter tending to retract most of the way to their original dimension when a stretching force is released. The stretching force can be any reasonable force sufficient to extend the material to between 125% of its original dimension, and its maximum stretched dimension in the selected direction (e.g., the cross direction) without rupturing it.

"Film" refers to a thermoplastic film made using a film extrusion and/or foaming process, such as a coating, cast film or blown film extrusion process. For the purposes of the present invention, the term includes breathable microporous and inherently breathable films that act as liquid barriers.

"Inelastic" refers both to materials that do not stretch by 25% or more and to materials that stretch by that amount but do not retract by more than 30%. Inelastic materials include extendible materials, as defined above, as well as materials that do not extend, e.g., which tear when subjected to a stretching force.

"Layer" when used in the singular can have the dual meaning of a single element or a plurality of elements.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter the meltblown fibers carried by the high velocity gas stream are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Necked" or "neck stretched" are interchangeable terms and refer to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al.

"Nonwoven" and "nonwoven web" refer to fibrous materials and webs of fibrous material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecules. These configurations include, but are not limited to isotactic, syndiotactic and atactic symmetries.

"Rugosities" refers to thin, narrow grooved or channeled wrinkles in an inelastic film layer.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as described, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338, 992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally are not tacky when they are deposited onto a collecting surface. Spunbond fibers are generally continuous and often have average deniers larger than about 0.3, more particularly, between about 0.6 and 10.

These terms may be defined with additional language in the remaining portions of the specification.

DETAILED DESCRIPTION OF THE PRESENTLY PREFERRED EMBODIMENTS

The present invention is directed to a breathable laminate that can extend in all directions in an x/y plane. The material of the present invention is particularly suitable for use as an outer cover for disposable absorbent articles. Examples of such suitable articles include diapers, training pants, incontinence products, swim wear, other personal care or health care garments, or the like.

Figure 2:
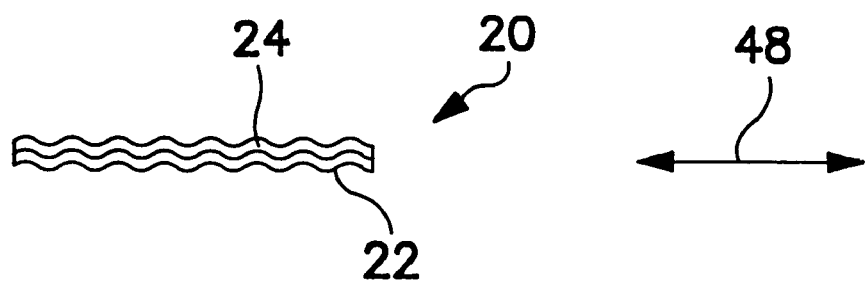
FIG. 2 is a cross-sectional view of a biaxially extendible, breathable laminate, taken along line 2—2 of FIG. 1.

Referring to FIGS. 1 and 2, there is shown a top view and a cross-sectional view, respectively, of a biaxially extendible, breathable laminate 20. The laminate 20 is made up of a film layer 22 and a nonwoven web layer 24. The nonwoven web layer 24 is neck-stretched in the machine direction to impart cross direction extendibility. The film layer 22 is extendible in a cross direction. Both the nonwoven layer 24 and the film layer 22 are creped to impart machine direction extendibility.

Figure 3:
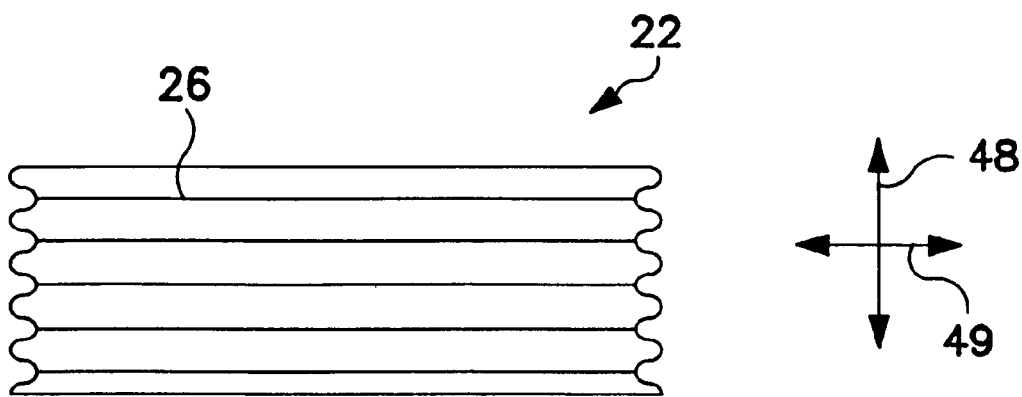
FIG. 3 is a top view of a film layer having striated rugosities.

Suitably, the film 22 can either be made of an extendible polymer that is extendible in the cross direction or can be an inelastic, striated film having striated rugosities in the machine direction which permit the film 22 to extend in the cross direction. In either case, the film 22 is suitably a breathable, microporous or inherently breathable film. The film layer 22 alone having striated rugosities 26 is shown in FIG. 3.

The term "cross direction," as used herein, refers to the width of a material in a direction generally perpendicular to the direction in which it is produced, as opposed to "machine direction," which refers to the length of a material in the direction in which it is produced. For reference, arrow 49 depicts the machine direction in FIGS. 1 and 3, while arrow 48 depicts the cross direction in FIGS. 1–3. The machine direction in FIG. 2 extends into and out of the page.

The breathability of the unstretched laminate 20, expressed as water vapor transmission rate (WVTR), is essentially equal to the breathability of the film layer 22 when the film 22 and the nonwoven web 24 are initially bonded. The nonwoven layer 24 is typically open and porous and does not significantly affect the breathability of the laminate 20. The WVTR is a function of both film thickness and film composition. The film layer 22 suitably can deliver moderate breathability, expressed as WVTR, in a range of about 500 to 30,000 grams/m$^2$-24 hours using the Mocon WVTR test procedure described below. Suitably, the moderate WVTR of the film layer 22 is at least about 500 grams/m$^2$-24 hours, even more suitably at least about 750 grams/m$^2$-24 hours, most suitably at least about 1000 grams/m$^2$-24 hours.

In an embodiment including an inelastic, striated film 22, the inelastic, striated film 22 can include a filler component extruded within a polymer component. The filler component initiates the formation of voids surrounding the filler particles upon stretching of the film 22 in the machine direction. The voids impart breathability to the film 22 by creating a tortuous path of thin membranes through which water vapor, but not liquid water, can pass.

As used herein, a "filler" is meant to include particulates and/or other forms of materials which can be added to the polymer blend prior to film extrusion, and which will not chemically interfere with or adversely affect the extruded film 22 and, further, which can be uniformly dispersed throughout the film 22. Generally the filler component will be in particulate form with average particle sizes in the range of about 0.1 to about 7 micrometers, desirably from about 0.1 to about 4 micrometers. As used herein the term "particle size" describes the largest dimension or length of the filler component. Both organic and inorganic fillers are contemplated for use with the present invention provided they do not interfere with the film forming process and/or subsequent laminating processes. Examples of fillers include calcium carbonate (CaCO$_3$), various clays, silica (SiO$_2$), alumina, barium sulfate, talc, magnesium sulfate, titanium dioxide, zeolites, aluminum sulfate, cellulosic powders, diatomaceous earth, gypsum, magnesium carbonate, barium carbonate, kaolin, mica, carbon, magnesium oxide, aluminum hydroxide, pulp powder, wood powder, cellulose derivatives, polymeric particles, chitin and chitin derivatives. The filler particles optionally may be coated with a fatty acid, such as stearic acid or behenic acid, and/or other material in order to facilitate the free flow of the particles (in bulk) and their ease of dispersion into the polymer. For example, using calcium carbonate filler with a density of about 2.8 grams per cubic centimeter, the filled film 22 will usually contain at least about 15% filler based upon the total volume of the film layer 22, more desirably from about 20% to about 65% by volume.

Suitable polymers for the polymer component include, but are not limited to, non-elastic extrudable polymers such as polyolefin or a blend of polyolefins, cellulose hydrate (cellophane), and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Other suitable polymers include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Metallocene process catalysts include bis(n-butylcyclopentadienyl) titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

Such metallocene polymers are available from Exxon-Mobil Chemical Company of Baytown, Tex. under the trade name EXXPOL® for polypropylene based polymers and EXACT® for polyethylene based polymers. Dow Chemical Company of Midland, Mich. has polymers commercially available under the name ENGAGE®. Preferably, the metallocene polymers are selected from copolymers of ethylene and 1-butene, copolymers of ethylene and 1-hexene, copolymers of ethylene and 1-octene and combinations thereof. In general, the metallocene-derived ethylene-based polymers of the present invention have a density of at least 0.900 g/cc.

The inelastic, striated film 22 may be a multi-layered film layer which may include a core layer and one or more skin layers on either side of the core layer. When more than one skin layer is present, it is not a requirement that the skin layers be the same. Any of the polymers discussed above are suitable for use as a core layer of a multi-layered film. Any of the fillers discussed above are suitable for use in any film layer.

The skin layer typically includes extrudable thermoplastic polymers and/or additives which provide specialized properties to the striated, inelastic film layer 22. Thus, the skin layer may be made from polymers which provide such properties as antimicrobial, barrier, water vapor transmission, adhesion and/or antiblocking properties. The polymers are thus chosen for the particular attributes desired. Examples of possible polymers that may be used alone or in combination include homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU), and olefinic thermoplastic elastomers which are multistep reactor products wherein an amorphous ethylene propylene random copolymer is molecularly dispersed in a predominately semicrystalline high polypropylene monomer/low ethylene monomer continuous matrix. The skin layer can be formed of any semicrystalline or amorphous polymer, including one that is slightly elastic and that will undergo permanent deformation at the stretch percentage that the laminate will undergo. However, the skin layer is generally a polyolefin such as polyethylene, polypropylene, polybutylene or an ethylene-propylene copolymer, but may also be wholly or partly a polyurethane, a polyamide such as nylon, a polyester such as polyethylene terephthalate, a polyvinylidene fluoride, a polyacrylate such as poly(methyl methacrylate)(only in blends) and the like, and blends thereof.

This inelastic, striated film 22 can be bonded to the nonwoven web 24. The nonwoven web 24 is air-permeable and can be formed from any suitable process, including bonded carded web processes, meltblowing processes and spunbonding processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91). The nonwoven web of the present invention suitably has a basis weight of 10 to 90 gsm, more suitably 20 to 60 gsm.

The nonwoven web 24 is suitably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof.

Suitable fibers for forming the nonwoven web 24 include natural and synthetic fibers as well as bicomponent, multicomponent, and shaped polymer fibers. A plurality of neckable materials may also be used. Examples of such materials can include, for example, spunbond/meltblown composites and spunbond/meltblown/spunbond composites such as are taught in U.S. Pat. No. 4,041,203 issued to Brock et al., which is herein incorporated by reference.

The nonwoven web 24 can be bonded so as to impart a discrete bond pattern with a prescribed bond surface area. This is known as thermal point bonding. Thermal point bonding involves passing a web of fibers to be bonded between a heated calender or patterned roll and an anvil roll. The calender roll is patterned so that the entire nonwoven web is not bonded across its entire surface. If too much bond area is present on the nonwoven web, it will break before it necks. If there is not enough bond area, then the nonwoven web will pull apart. Typically, the percent bonding area useful in the present invention ranges from around 5% to around 40% of the area of the nonwoven web. Many patterns for calender rolls have been developed. As will be understood by those skilled in the art, bond area percentages are, of necessity, described in approximations or ranges since bond pins are normally tapered and wear down over time.

There are a number of discrete bond patterns which may be used. An example of one bond pattern is a "wire weave" pattern, shown in FIG. 4. The wire weave bond pattern 28 includes square-shaped nonwoven web pattern elements. Each pattern element can be defined by four ellipticalshaped point bonds 30. The side length of each pattern element (representing the center-to-center distance between adjacent bonds) can be about 0.057 inch. Each bond 30 may have a length of about 0.031 inch and a width of about 0.016 inch. The bond pattern 28 can be applied either evenly or unevenly to the nonwoven web 24. An evenly applied bond pattern 28 contributes to more consistent material properties across the surface of the resulting laminate 20, while an unevenly applied bond pattern 28 can affect material properties such as the level of retractive force. The nonwoven web suitably has a post-necked basis weight of about 10-30 grams per square meter (gsm).

As mentioned, the nonwoven layer 24 is neck-stretched in the machine direction, thereby imparting cross directional extendibility to the material. The process of necking is described in U.S. Pat. No. 5,226,992 issued to Morman, hereby incorporated by reference.

Laminating the film layer 22 to the nonwoven layer 24 may be carried out by typical methods known in the art, including adhesive bonding, point bonding and sonic welding. The use of inelastic and/or elastic adhesives for the adhesive bonding is suitable for this invention. An example of a suitable adhesive is a meltblown adhesive containing 54.5–57.5% by weight petroleum hydrocarbon resins; 18.5–21.5% by weight of a mixture of several mineral oils; 22.5–27.5% by weight of styrene-butadiene-styrene block copolymers; 0.1–0.9% by weight polyethylene and/or ethylene vinyl acetate; and 0.2–1.8% by weight antioxidants and stabilizers. Another specific example of a suitable adhesive is NS 34-5610, available from National Starch & Chemical Co. The adhesive can be applied molten to either the film 22 or the web 24 using a melt blowing process, at an add-on level of about 2 to 5 gsm. The resulting adhesive coverage is intermittent, and occupies about 5 to 40% of the interface between the film 22 and nonwoven web 24.

When the film layer 22 and nonwoven layer 24 are bonded through the use of heat and/or pressure, a laminating device, such as laminating rollers, can be used. The laminating rollers may be heated and point bonding may be used. The temperature at which the laminating rollers are heated depends on the properties of the film 22 and/or the nonwoven 24, but is usually in the range of 200 to 275° F. (93 to 135° C.). The laminating rollers may each be smooth or patterned or one roll may be smooth while the other roll is patterned. If one of the rolls is patterned it will create a discrete bond pattern with a prescribed bond surface area for the resultant laminate 20.

To make the laminate 20 including the inelastic, striated film 22 and nonwoven web 24, the film 22 is first stretched in the machine direction to 2–5 times its original, unstretched length using two or more nipped pairs of heated draw rollers, with each subsequent pair turning faster than each preceding pair. The stretching is carried out to impart breathability to the film 22. One or both draw rollers in each pair may be heated, so that the film 22 experiences a stretching temperature of 150–200° Fahrenheit (F.). The stretched film 22 has a thickness of less than 50 mils.

The stretched film 22 is then laminated to the nonwoven web 24 with the machine direction of the film 22 substantially aligned with the machine direction of the web 24. When adhesively bonding the film 22 to the nonwoven web 24, a molten adhesive is applied to either the film 22 or the web 24, and the film 22 and web 24 are brought together under light pressure (less than 50 lb/linear inch) using a pair of unheated smooth nip rollers, to form the laminate 20. At that point, the adhesive is still warm enough to effect bonding between the film 22 and web 24.

The laminate 20 is then stretched in the machine direction of the film 22 and the web 24, by passing it through a pair of unheated stretch nip rollers that turn at greater speeds than the laminating nip rollers. An oven set at 200–280° F. may be positioned between the pairs of nip rollers, to aid in necking and heat setting the laminate 20. The laminate 20 is stretched in this manner to about 1.15–1.20 times its length immediately after lamination. This causes necking of the nonwoven web 24 to 60–75% of its initial width. This also causes further stretching of the film 22, to about 2.5–7 times its original length occurring before the pre-lamination stretching. Also, because the film 22 is laminated to the web 24, the further stretching causes the film 22 to gather in the cross direction, resulting in the formation of striated rugosities 26 (thin, narrow grooved or channeled wrinkles) in the film 22 (FIG. 3). The basis weight of the laminate 20 increases as a result of the stretching.

Once the laminate 20 is formed, the laminate 20 is then creped with a creping adhesive to achieve machine direction extendibility. Suitable creping adhesives include without limitation aqueous-based styrene butadiene adhesives, neoprene, polyvinyl chloride, vinyl copolymers, polyamides, and ethylene vinyl terpolymers. The presently preferred adhesive material is an acrylic polymer emulsion sold by the B. F. Goodrich Company under the trade name HYCAR®. The use of an elastomeric creping adhesive may impart some retractive force to the laminate 20. Any suitable method of creping can be used. For example, the nonwoven web layer 24 can be at least partially coated with an elastomeric creping adhesive on a side opposite the film layer 22, so that about 5–100% (preferably 10–70%) of the total surface area on that side is coated, and about 0–95% (preferably 30–90%) of the area is uncoated. The creping adhesive can be applied either evenly or unevenly across the nonwoven layer 24. An evenly applied creping adhesive contributes to more consistent material properties across the surface of the resulting laminate 20, while an unevenly applied creping adhesive can affect material properties such as the level of retractive force.

Figure 4:
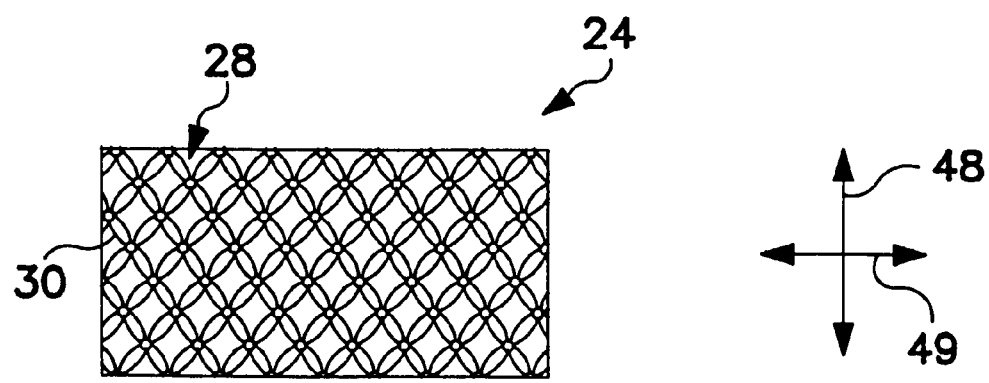
FIG. 4 is a top view of a nonwoven layer having a wire weave bond pattern.

The nonwoven web 24 possesses interfilament bonding, in the form of the bond pattern 28 which is imparted during manufacture of the nonwoven web 24 (FIG. 4). The elastomeric creping adhesive penetrates the nonwoven web 24 to some extent in the coated areas, causing increased interfilament bonding in those areas. The at least partially coated side of the nonwoven web 24 can then be placed against a creping surface, such as a creping drum, and can be peelably bonded to the creping surface.

The creping surface is preferably heated, and is moved (e.g. rotated) in a machine direction. The speed of the rotation of the creping surface depends on the composition of the material being creped, but for the embodiments described herein, a suitable range of rotation speed is roughly 175 to 250 feet per minute. Suitably, the creping surface moves fast enough to decrease the machine direction length of the laminate 20 by roughly one-half to produce a laminate with 100% machine direction elongation. As the creping surface moves, the leading edge of the laminate 20 bonded to the surface can be creped off using a doctor blade. The doctor blade penetrates the adhesive coating underneath the web and lifts the laminate off the drum, resulting in laminate bending in the cross direction. Alternatively, the creping adhesive can be applied to a surface of the film 22 opposite the nonwoven layer 24. Other examples of creping are taught in U.S. Pat. No. 4,810,556, issued to Kobayashi et al.; U.S. Pat. No. 6,197,404, issued to Varona and entitled "Creped Nonwoven Materials;" and U.S. Pat. No. 6,150,002, issued to Varona and entitled "Creped Nonwoven Liner With Gradient Capillary Structure;" each of which is hereby incorporated by reference. By creping just one side of the laminate 20, the entire thickness of the laminate 20, including both the film layer 22 and the nonwoven layer 24, can be creped.

The resulting material 20 of this embodiment, therefore, includes a flat nonwoven layer 24 laminated to an inelastic film layer 22 having striated rugosities 26 in the machine direction, with both the nonwoven layer 24 and the film layer 22 together having undulations in the cross direction, such that a "valley" in the undulation extends across the material 20 in the cross direction. Thus, the resulting laminated material 20 can extend in all directions in an x/y plane.

The laminated material 20 of this embodiment is breathable to water vapor because the machine direction stretching of the film 22 causes voids to form around the calcium carbonate particles. When measured using INDA Test Method IST-70.4-99 (the "Mocon" test), the pre-stretched laminate 20 has a water vapor transmission rate (WVTR) of greater than 1000 grams/m$^2$-24 hours, and often greater than 2000 grams/m$^2$-24 hours. Yet both the film 22 and laminate 20 are substantially impermeable to liquid water.

In another embodiment of the invention, the film 22 can be a single-layer cross-direction extendible film rather than the inelastic, striated film of the previous embodiment. In this embodiment, the film 22 can be made from an extendible polymer. The extendible polymer permits the film 22 (along with the necked nonwoven web 24) to extend in the cross direction.

The extendible film 22 can include a single microporous or inherently breathable core layer, or one or more skin layers in addition to the core layer, as described in the previous embodiment. As in the inelastic, striated film, the extendible microporous film also includes a filler component extruded within a polymer, but in this embodiment the polymer is extendible. The filler component described in the previous embodiment is suitable for use in this embodiment as well.

The extendible polymer used in this embodiment can be formed from any extendible film-forming thermoplastic polymer. Examples of suitable polymers include without limitation certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other extendible polymers include very low density polyethylene (VLDPE), which is an ethylene-alpha olefin copolymer having a density less than 0.900 grams/cm$^3$, preferably about 0.870–0.890 grams/cm$^3$. Preferred VLDPE's are single-site catalyzed. Other extendible polymers include random propylene-alpha olefin copolymers containing more than 10% by weight of a $C_2$ or $C_4$-$C_{12}$ comonomer, preferably about 15–85% by weight of the comonomer, with ethylene being a preferred comonomer.

The extendible polymer should be of a type and amount that causes the film 22 to have cross-directional extendibility of at least about 25% of an initial, unstretched width when a stretching force is applied. When the stretching force is relaxed, the film 22 should not by itself cause the laminate to retract by more than 30% of the difference between the stretched width and the initial, unstretched width. Any further retraction of a laminate containing the film 22 may be caused by an elastomeric adhesive and/or elastomeric component forming part of the laminate 20. Preferably, the film 22 should have cross-directional extendibility of at least about 35% (e.g., 35–300%) of the initial width, more preferably at least about 50% (e.g., 50–200%). The extendible polymer may be blended with a non-extendible polymer so long as the film 22 has the needed extendibility. Preferred polymers for the film 22 are single-site catalyzed ethylene copolymers and flexible polyolefins (FPOs) as described above.

The polymer composition, filler content, filler particle size and degree of stretching are factors which help determine the breathability and liquid barrier of the extendible film 22 in the laminate 20. Generally, the extendible film 22 will be less than about 50 microns thick, preferably less than about 30 microns thick, most preferably less than about 20 microns thick. The film 22 may be uniaxially stretched to about 1.1–7.0 times its original length to cause breathability, preferably to about 1.5–6.0 times its original length, most preferably to about 2.5–5.0 times its original length. The film 22 may alternatively be biaxially stretched using conventional techniques familiar to persons skilled in the art. Preferably, the film 22 is uniaxially stretched in its machine direction, and is laminated to the nonwoven web 24 with the machine direction of the film 22 aligned with the machine direction of the web 24. Stretching temperatures may range from about 38–150° C. depending on the specific polymers employed, and are preferably about 70–95 ° C. The breathable extendible film 22 can be prepared by cast or blown film coextrusion of the layers, by extrusion coating, or by any conventional layering process.

The laminated material 20 of this embodiment includes the extendible film 22 and a nonwoven web 24, bonded together and creped. The nonwoven web 24, necking of the nonwoven web 24, bonding process, bonding materials, and creping process can suitably be the same as in the previous embodiment.

The resulting material 20 of this embodiment, therefore, includes a flat nonwoven layer 24 laminated to a cross-direction extendible film layer 22, with both the nonwoven layer 24 and the film layer 22 together having undulations in the cross direction. Thus, the resulting laminated material 20 can extend in all directions in an x/y plane.

In an alternative embodiment of the invention, the nonwoven web 24 can be creped prior to bonding the film layer 22 to the nonwoven layer 24 rather than creping the laminated material 20. In this case, the film must also be extendible in the machine direction.

When used to make an outer cover of an absorbent garment, portions of the laminate 20 (i.e., corresponding to the front and back waist regions in a pant-like garment) may be extended by 30–200% in the cross direction. The cross-directional stretching causes the necked nonwoven web 24 to return toward its original, un-necked configuration, and causes the film 22 to extend in the cross direction by 30–200% (to 130–300%) of its initial width. The laminate 20 can be readily extended in the cross direction, by hand, because the film 22 is made from an extendible polymer composition.

In general, the laminated material 20 of the invention can suitably be extended by about 30 to 200% in the cross direction, more suitably by about 40 to 170%, most suitably by about 50 to 150%. Similarly, the creping of the laminate 20 enables the laminated material 20 of the invention to be extended by about 30 to 200% in the machine direction, more suitably by about 40 to 170%, most suitably by about 50 to 150%.

The extendible film 22 and laminate 20 of this embodiment have variable breathability to water vapor, as measured by INDA Test Method IST-70.4-99. Before the laminate 20 is stretched in the cross direction, it typically has a WVTR of less than 1000 grams/m$^2$-24 hours. Following a 25% stretch in the cross direction, the portions of the laminate affected by the stretch typically have a much higher WVTR, of at least 4,000 grams/m$^2$-24 hours. Whether or not stretched in the cross direction, the film 22 and laminate 20 are substantially impermeable to liquid water.

Regardless of whether the EOC laminate 20 is made using an inelastic, striated film or an extendible film, the film 22 may retract by 2–30% of its stretched length in the machine direction, after being bonded to the nonwoven web 24. This retraction may cause the web 24 to have a three-dimensional surface topography characterized by loops or pillows. In each EOC laminate 20, the breathable film 22 has a thickness in a range of about 0.2 to 4.0 mil.

As mentioned, the resulting laminate 20 of the invention has low retractive force. The term "low retractive force" refers to retractive forces that are not strong enough to retract the laminate more than about 30% from an extension of about 30% to about 200%.

To achieve greater retractive force in the laminate 20 than is provided by the creping adhesive, an elastomeric component can alternatively be attached to either the film layer 22 or the nonwoven layer 24 or between the film layer 22 and the nonwoven layer 24. The elastomeric component can be in the form of, for example, films, fibers, or scrims of polyurethane, polyetherester, polyetheramide, or styrene-isoprene-styrene block copolymers. The elastomeric component can be applied in a pattern, such as in rows or columns, such that the laminate 20 can have high retractive force in one direction and little or no retractive force in another direction. Any of these elastomeric components can be bonded to the laminate 20 using conventional means, including adhesive bonding, thermal bonding, or ultrasonic bonding.

EXAMPLES

Two samples of the present invention were prepared, along with two control samples. A first sample ("Inelastic 50/50") included an inelastic, striated film, namely a 20-inch breathable stretch-thermal laminate available under the trade designation XP-1885, containing a filler, such as calcium carbonate, that was stretched 3.6 times in the machine direction to make it microporous and breathable, and adhesively bonded to a 0.4 osy wire-weave polypropylene spunbond using H2525A adhesive, resulting in 3 gsm add-on. The unwind speed was 50 feet per minute (FPM), while the lamination speed was 184 FPM. The entire laminate was then stretched 1.12 times in the machine direction that caused the laminate to neck to 65% of its original width. The resulting total film draw in the laminate was four. The machine direction stretching caused the spunbond to narrow which forced the film attached to the spunbond to form machine-direction striated rugosities. This laminate was then creped using a drum temperature of 240 degrees Fahrenheit with A-Flob 15 creping adhesive, available from Air Products and Chemicals, Inc., of Allentown, Pa. The take-off speed from the creping drum was roughly one-half the speed of the drum (125 feet per minute versus 225 feet per minute). The add-on rate of the creping adhesive was about 0.6%, but what actually ended up on the material was much less, closer to about 0.1% or less. A control sample ("Inelastic Control") was the same as the Inelastic 50/50 sample but without the creping, thus the basis weight of the Inelastic 50/50 was approximately twice the basis weight of the Inelastic Control.

A second sample ("Extendible 50/50") of cross-direction extendible, breathable laminate was produced by adhesively laminating a necked spunbond web to a cross-direction extendible films The spunbond had been necked enough to give the laminate the desired amount of cross-direction extendibility. The film was a polyolefin film that was calcium carbonate filled and was stretched before lamination enough to give the laminate the desired breathability.

Another control sample ("Extendible Control") was roughly the same as the Extendible 50/50 sample but without the creping, thus the basis weight of the Extendible 50/50 was approximately twice the basis weight of the Extendible Control. More particularly, the Extendible Control was a commercially made 0.4 osy spunbond with a wire weave thermal bonding pattern necked to about two-thirds of its original width and laminated to a commercially produced breathable stretched film. The breathable stretched film was a three-layer A-B-A cast film sold as Huntsman Type 1885, available from Huntsman Packaging Corp., 199 Edison Drive, Washington, Ga. 30763. The film had a core layer containing 42% by weight (69% by volume) Ziegler-Natta catalyzed linear low density polyethylene. The polyethylene had an octene comonomer, and a density of 0.918 grams/cm$^3$. The core layer also contained 58% by weight (31% by volume) of stearic acid-coated calcium carbonate particles having a mean diameter of about 1 micron and a top cut of 7 microns. The film had two skin layers, each containing a mixture of 50.4% by weight ethylene vinyl acetate (28% by weight vinyl acetate content), 45.1% by weight of a heterophasic combination of propylene-ethylene copolymers commercially known as Montell KS-357P catalloy, 4% by weight SUPER FLOSS diatomaceous earth made by McCullough and Benton, and 0.5% by weight B-900 antioxidant made by Ciba Specialties Company. The skin layers constituted about 3% of the total film thickness. The breathable stretched film was prestretched four times before being laminated to the necked spunbond using about one gram per square meter of Findley 2525A styrene-isoprene-styrene based adhesive, available from Ato-Findley Adhesives, Inc., of Wauwatosa, Wis. U.S.A.

All four samples were subjected to the following test:

Tensile Test: The tensile test measured strength and elongation or strain of a fabric when subjected to unidirectional stress according to ASTM Standard Test D 5034-95, as well as Federal Test Methods Standard No. 191A Method 5102-78. This test measured the strength in pounds and percent stretch while elongating the sample until it broke. Higher numbers indicate a stronger and/or more stretchable fabric, respectively. The term "peak load" means the maximum load or force, expressed in pounds, required to elongate a sample to break or rupture in a tensile test. The term "strain" or "percent stretch" means the increase in length of a sample during a tensile test expressed as a percentage. Values for peak load and strain at peak load were obtained using a width of fabric of 3×6 in. (76×152 mm), a 3 in. (76 mm) clamp width, a gauge length of 3 in. (76 mm), and a constant rate of extension of 12 inches/min. (305 min/min.), where the entire sample width was gripped in the clamps. The specimen was clamped, for example, in an 1130 Instron, available from the Instron Corporation, or a Thwing-Albert Model INTELLECT II available from the Thwing-Albert Instrument Co., 10960 Dutton Rd., Philadelphia, Pa. 19154, and the unit was zeroed, balanced and calibrated according to the standard procedure.

Material properties and results from the tensile test for the four samples are shown in Table 1 below. Because the test samples, Inelastic 50/50 and Extendible 50/50, have roughly twice the basis weight as the respective control samples due to creping, Table 2 shows the results from the tensile test normalized by the basis weights of the samples. The difference in basis weight between the test samples and control samples affects the material properties being tested in the CD and does not appreciably affect the material properties being tested in the MD since the basis weight difference is caused by creping in the MD.

As can be seen in Tables 1 and 2, Inelastic 50/50 and Extendible 50/50 both have a considerably low modulus in both the MD and the CD compared to the respective control samples. The peak load in the CD of both Inelastic 50/50 and Extendible 50/50 was roughly equal to the respective control samples once normalized by the basis weight, as shown in Table 2. However, the peak load in the MD of both Inelastic 50/50 and Extendible 50/50 was noticeably lower than the respective control samples in both Table 1 and Table 2. The peak strain in the CD of both Inelastic 50/50 and Extendible 50/50 was roughly the same as the peak strain in the CD of the control samples, as shown in Table 2. The peak strain in the MD of both Inelastic 50/50 and Extendible 50150 was noticeably higher than the peak strain in the MD of the respective control samples, as shown in Table 1 and and Table 2. As can be seen in Table 1 and Table 2, the peak strain was represented in terms of percent elongation. The percent elongation was determined by dividing the difference between the final length and the initial length by the initial length, and multiplying the quotient by 100. Since the peak strain values were in terms of percentages, the peak strain values were not normalized by basis weight in Table 2.

TABLE 1

Material Properties

| Sample | Basis Weight (gsm) | Modulus MD (psi) | Modulus CD (psi) | Peak Load MD (grams) | Peak Load CD (grams) | Peak Strain MD (% elongation) | Peak Strain CD (% elongation) |
| --- | --- | --- | --- | --- | --- | --- | --- |
| Inelastic Control | 51.9 | 4727 | 519.8 | 16815 | 3069 | 50.7 | 114.7 |
| Inelastic 50/50 | 97.2 | 284 | 138.1 | 12275 | 6082 | 170.4 | 120.4 |
| Extendible Control | 34.2 | 16897 | 1896 | 15141 | 2555 | 30.2 | 136.9 |

TABLE 1-continued

Material Properties

| Sample | Basis Weight (gsm) | Modulus MD (psi) | Modulus CD (psi) | Peak Load MD (grams) | Peak Load CD (grams) | Peak Strain MD (% elongation) | Peak Strain CD (% elongation) |
|---|---|---|---|---|---|---|---|
| Extendible 50/50 | 77.6 | 395 | 423 | 11584 | 5816 | 169.8 | 146 |

TABLE 2

Material Properties Normalized by Basis Weight

| Sample | Basis Weight (gsm) | Modulus MD (psi/gsm) | Modulus CD (psi/gsm) | Peak Load MD (grams/gsm) | Peak Load CD (grams/gsm) | Peak Strain MD (% elongation) | Peak Strain CD (% elongation) |
|---|---|---|---|---|---|---|---|
| Inelastic Control | 51.9 | 91.1 | 10.0 | 324.0 | 59.1 | 50.7 | 114.7 |
| Inelastic 50/50 | 97.2 | 2.9 | 1.4 | 126.3 | 62.6 | 170.4 | 120.4 |
| Extendible Control | 34.2 | 494.1 | 55.4 | 442.7 | 74.7 | 30.2 | 136.9 |
| Extendible 50/50 | 77.6 | 5.1 | 5.5 | 149.3 | 74.9 | 169.8 | 146 |

During the above tensile testing, individual force data points (measured in grams) were taken at specified elongations in both the machine direction and the cross direction and are shown below in Tables 3 and 4. Table 5 is normalized by the basis weights of the samples and is in grams/gsm.

TABLE 3

Machine Direction Elongation

| % Elongation MD | Inelastic Control | Inelastic 50/50 | Extendible Control | Extendible 50/50 |
|---|---|---|---|---|
| 1% | 635 | 178 | 992 | 268 |
| 2% | 1216 | 354 | 2492 | 487 |
| 3% | 1747 | 526 | 3924 | 688 |
| 4% | 2297 | 684 | 5204 | 859 |
| 5% | 2915 | 849 | 6347 | 1024 |
| 10% | 7040 | 1579 | 10177 | 1544 |
| 30% | 14785 | 3159 | 14692 | 2413 |
| 50% | 14742 | 3740 | | 2837 |
| 75% | | 4316 | | 3426 |
| 100% | | 5809 | | 5215 |
| 170% | | 12275 | | 11584 |

As can be seen in Table 3, the forces required to elongate the samples of the present invention were considerably lower than those required to extend the controls. Further, the controls broke at a much lower extension than the inventive samples, as also can be seen in Table 1.

TABLE 4

Cross Direction Elongation

| % Elongation CD | Inelastic Control | Inelastic 50/50 | Extendible Control | Extendible 50/50 |
|---|---|---|---|---|
| 1% | 47 | 24 | 65 | 38 |
| 2% | 68 | 64 | 187 | 149 |
| 3% | 87 | 111 | 318 | 326 |
| 4% | 106 | 171 | 448 | 598 |
| 5% | 125 | 226 | 525 | 819 |
| 10% | 173 | 438 | 680 | 1414 |
| 30% | 345 | 1079 | 807 | 1777 |
| 50% | 1114 | 1798 | 887 | 1978 |
| 75% | 2156 | 3746 | 1210 | 2764 |
| 100% | 2839 | 5324 | 1896 | 4150 |

TABLE 5

Normalized Cross Direction Elongation

| % Elongation CD | Inelastic Control | Inelastic 50/50 | Extendible Control | Extendible 50/50 |
|---|---|---|---|---|
| 1% | 0.9 | 0.2 | 1.9 | 0.5 |
| 2% | 1.3 | 0.7 | 5.5 | 1.9 |
| 3% | 1.7 | 1.1 | 9.3 | 4.2 |
| 4% | 2.0 | 1.8 | 13.1 | 7.7 |
| 5% | 2.4 | 2.3 | 15.4 | 10.6 |
| 10% | 3.3 | 4.5 | 19.9 | 18.2 |
| 30% | 6.6 | 11.1 | 23.6 | 22.9 |
| 50% | 21.5 | 18.5 | 25.9 | 25.5 |
| 75% | 2156 | 3746 | 1210 | 2764 |
| 100% | 2839 | 5324 | 1896 | 4150 |

As explained above, the difference in basis weights between the test samples and the control samples affects the CD properties being tested. Therefore, the values in Table 4 have been normalized by the basis weights of the samples, listed in Table 1, and the normalized values appear in Table 5. As can be seen in Table 5, the extendibility of the inventive samples was not significantly changed due to the creping process.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Test Procedure For Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. A sensor generates a signal proportional to the vapor content of the gas stream. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}{}_{test\ material} = TR^{-1}{}_{test\ material,\ a\ guardfilm,\ airgap} - TR^{-1}{}_{guardfilm,\ airgap}$$

Calculations:

WVTR: The calculation of the WVTR uses the formula:

$$WVTR = Fp_{sat}(T)RH/(Ap_{sat}(T)(1-RH))$$

where:

F=The flow of water vapor in cc/min., $P_{sat}(T)$=The density of water in saturated air at temperature T, RH=The relative humidity at specified locations in the cell, A=The cross sectional area of the cell, and, $P_{sat}(T)$=The saturation vapor pressure of water vapor at temperature T.

We claim:

1. A laminated material extendible in a first direction and in a second mutually perpendicular direction, comprising:
   a film having striated rugosities in the first direction and undulations in the second mutually perpendicular direction;
   a nonwoven web bonded to the film, the nonwoven web having undulations in the second mutually perpendicular direction; and
   a creping adhesive applied to the laminated material.

2. The laminated material of claim 1, wherein the film comprises an inelastic film.

3. The laminated material of claim 1, wherein the film comprises a breathable, microporous film.

4. The laminated material of claim 1, wherein the nonwoven web comprises a spunbond web.

5. The laminated material of claim 1, wherein the nonwoven web is adhesively bonded to the film.

6. The laminated material of claim 1, wherein the nonwoven web is thermally bonded to the film.

7. A laminated material extendible in a first direction and in a second mutually perpendicular direction, comprising:
   a film having undulations in the second direction and extendibility in the second direction;
   a nonwoven web bonded to the film, the nonwoven web having undulations in the second direction; and
   a creping adhesive applied to the laminated material.

8. The laminated material of claim 7, wherein the film comprises an extendible polymer that is extendible in the second direction.

9. The laminated material of claim 7, wherein the nonwoven web comprises a spunbond web.

10. The laminated material of claim 7, wherein the nonwoven web is adhesively bonded to the film.

11. The laminated material of claim 7, wherein the nonwoven web is thermally bonded to the film.

12. A laminated material extendible in a first direction and in a second mutually perpendicular direction, comprising:
    a film extendible in the second direction;
    a nonwoven web neck-stretched in the first direction and adhesively creped in the first direction; and
    an adhesive bonding the film to the nonwoven web.

13. The laminated material of claim 12, wherein the film comprises a breathable, microporous film.

14. The laminated material of claim 12, wherein the film comprises an inelastic film adhesively creped in the first direction and having rugosities in the second direction.

15. The laminated material of claim 12, wherein the film comprises an extendible polymer that is extendible in the second direction.

16. The laminated material of claim 12, wherein the first direction comprises a machine direction and the second direction comprises a cross direction.

17. The laminated material of claim 12, wherein an elastomeric creping adhesive is unevenly applied to at least one of the film and the nonwoven web.

18. The laminated material of claim 12, wherein a bond pattern is unevenly applied to the nonwoven web.

19. The laminated material of claim 12, further comprising an elastomeric film bonded to at least one of the extendible film and the nonwoven web.

20. The laminated material of claim 12, further comprising a plurality of elastomeric fibers bonded to at least one of the extendible film and the nonwoven web.

21. The laminated material of claim 12, further comprising an elastomeric foam bonded to at least one of the extendible film and the nonwoven web.

22. The laminated material of claim 12, further comprising an elastomeric scrim bonded to at least one of the extendible film and the nonwoven web.

23. The laminated material of claim 12, wherein the laminated material can be extended by about 30% to about 200% in the first direction.

24. The laminated material of claim 12, wherein the laminated material can be extended by about 40% to about 170% in the first direction.

25. The laminated material of claim 12, wherein the laminated material can be extended by about 50% to about 150% in the first direction.

26. The laminated material of claim 12, wherein the laminated material can be extended by about 30% to about 200% in the second direction.

27. The laminated material of claim 12, wherein the laminated material can be extended by about 40% to about 170% in the second direction.

28. The laminated material of claim 12, wherein the laminated material can be extended by about 50% to about 150% in the second direction.

29. An absorbent article outer cover comprising the laminated material of claim 12.

30. A laminated material extendible in a first direction and in a second mutually perpendicular direction, comprising:
   an inelastic film creped in the first direction and having rugosities in the second direction;
   a nonwoven web neck-stretched in the first direction, creped in the first direction, and laminated to the film; and
   an elastomeric creping adhesive applied to a surface of at least one of the film and web.

31. The laminated material of claim 30, wherein the film comprises a breathable, microporous film.

32. The laminated material of claim 30, wherein the elastomeric creping adhesive is applied unevenly to at least one of the film and the nonwoven web.

33. The laminated material of claim 30, wherein a bond pattern is unevenly applied to the nonwoven web.

34. The laminated material of claim 30, further comprising an elastomeric film bonded to at least one of the inelastic film and the nonwoven web.

35. The laminated material of claim 30, further comprising a plurality of elastomeric fibers bonded to at least one of the inelastic film and the nonwoven web.

36. The laminated material of claim 30, further comprising an elastomeric foam bonded to at least one of the inelastic film and the nonwoven web.

37. The laminated material of claim 36, further comprising an elastomeric scrim bonded to at least one of the inelastic film and the nonwoven web.

38. The laminated material of claim 30, wherein the laminated material can be extended by about 30% to about 200% in the first direction.

39. The laminated material of claim 30, wherein the laminated material can be extended by about 40% to about 170% in the first direction.

40. The laminated material of claim 30, wherein the laminated material can be extended by about 50% to about 150% in the first direction.

41. The laminated material of claim 30, wherein the laminated material can be extended by about 30% to about 200% in the second direction.

42. The laminated material of claim 30, wherein the laminated material can be extended by about 40% to about 170% in the second direction.

43. The laminated material of claim 30, wherein the laminated material can be extended by about 50% to about 150% in the second direction.

44. An absorbent article outer cover comprising the laminated material of claim 30.

45. A laminated material extendible and recoverable in a first direction and in a second mutually perpendicular direction, comprising:
   an inelastic film adhesively creped in the first direction and having rugosities in the second direction;
   a nonwoven web neck-stretched in the first direction, adhesively creped in the first direction, and laminated to the film; and
   an elastomeric component attached to at least one of the film and the web.

46. The laminated material of claim 45, wherein the film comprises a breathable, microporous film.

47. The laminated material of claim 45, wherein an elastomeric creping adhesive is unevenly applied to at least one of the film and the nonwoven web.

48. The laminated material of claim 45, wherein a bond pattern is unevenly applied to the nonwoven web.

49. The laminated material of claim 45, wherein the elastomeric component comprises an elastomeric film.

50. The laminated material of claim 45, wherein the elastomeric component comprises a plurality of elastomeric fibers.

51. The laminated material of claim 45, wherein the elastomeric component comprises an elastomeric foam.

52. The laminated material of claim 45, wherein the elastomeric component comprises an elastomeric scrim.

53. The laminated material of claim 45, wherein the laminated material can be extended by about 30% to about 200% in the first direction.

54. The laminated material of claim 45, wherein the laminated material can be extended by about 40% to about 170% in the first direction.

55. The laminated material of claim 45, wherein the laminated material can be extended by about 50% to about 150% in the first direction.

56. The laminated material of claim 45, wherein the laminated material can be extended by about 30% to about 200% in the second direction.

57. The laminated material of claim 45, wherein the laminated material can be extended by about 40% to about 170% in the second direction.

58. The laminated material of claim 45, wherein the laminated material can be extended by about 50% to about 150% in the second direction.

59. An absorbent article outer cover comprising the laminated material of claim 45.

* * * * *

UNITED STATES PATENT AND TRADEMARK OFFICE
CERTIFICATE OF CORRECTION

PATENT NO. : 6,623,837 B2
DATED : September 23, 2003
INVENTOR(S) : Michael Tod Morman et al.

It is certified that error appears in the above-identified patent and that said Letters Patent is hereby corrected as shown below:

Column 18,
Line 4, replace the existing equation with the following equation:
-- $WVTR = F\rho_{sat}(T)RH/A\rho_{sat}(T)(1-RH)$ --
Line 8, replace "$P_{sat}(T)$" with -- $\rho_{sat}(T)$ --

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,623,837 B2
DATED : September 23, 2003
INVENTOR(S) : Michael Tod Morman et al.

It is certified that error appears in the above-identified patent and that said Letters Patent is hereby corrected as shown below:

<u>Column 18,</u>
Line 4, replace the existing equation with the following equation:
-- $WVTR = F\rho_{sat}(T)RH/A\rho_{sat}(T)(1-RH)$ --
Lines 8 and 13, replace "$P_{sat}(T)$" with -- $\rho_{sat}(T)$ --

This certificate supersedes Certificate of Correction issued September 28, 2004.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO.   : 6,623,837 B2
DATED        : September 23, 2003
INVENTOR(S)  : Michael Tod Morman et al.

It is certified that error appears in the above-identified patent and that said Letters Patent is hereby corrected as shown below:

<u>Column 18,</u>
Line 4, replace the existing equation with the following equation:
 -- $WVTR = F\rho_{sat}(T)RH/A\rho_{sat}(T)(1-RH)$ --
Line 8, replace "$P_{sat}(T)$" with -- $\rho_{sat}(T)$ --
Line 13, replace "$P_{sat}(T)$" with -- $p_{sat}(T)$ --

This certificate supersedes Certificate of Correction issued September 28, 2004 and December 21, 2004.

Signed and Sealed this

Twenty-sixth Day of July, 2005

JON W. DUDAS
*Director of the United States Patent and Trademark Office*